(12) United States Patent
Cho et al.

(10) Patent No.: US 9,675,324 B2
(45) Date of Patent: Jun. 13, 2017

(54) PORTABLE ULTRASONIC PROBE

(71) Applicant: SAMSUNG ELECTRONICS CO., LTD., Suwon-si (KR)

(72) Inventors: Kyung Il Cho, Seoul (KR); Bae Hyung Kim, Yongin-si (KR); Young Il Kim, Suwon-si (KR); Jong Keun Song, Yongin-si (KR); Seung Heun Lee, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 268 days.

(21) Appl. No.: 14/301,751

(22) Filed: Jun. 11, 2014

(65) Prior Publication Data
US 2014/0360274 A1 Dec. 11, 2014

(30) Foreign Application Priority Data
Jun. 11, 2013 (KR) .......................... 10-2013-0066432

(51) Int. Cl.
*G01N 29/24* (2006.01)
*A61B 8/00* (2006.01)
*G01N 29/06* (2006.01)

(52) U.S. Cl.
CPC .......... *A61B 8/4427* (2013.01); *A61B 8/4444* (2013.01); *A61B 8/546* (2013.01); *G01N 29/0654* (2013.01); *G01N 29/2431* (2013.01)

(58) Field of Classification Search
CPC ............ G01N 29/0654; G01N 29/2431; A61B 8/4444; A61B 8/546; A61B 8/4461; A61B 8/4455; A61B 8/4427; A61B 8/4438

USPC .......... 73/644, 632, 618, 626; 600/459, 457, 600/443
See application file for complete search history.

(56) References Cited

U.S. PATENT DOCUMENTS

| | | | |
|---|---|---|---|
| 5,722,412 A | 3/1998 | Pflugrath et al. | |
| 6,542,846 B1 * | 4/2003 | Miller | A61B 8/546 340/584 |
| 6,980,419 B2 * | 12/2005 | Smith | A61B 90/36 361/679.21 |
| 7,918,799 B2 * | 4/2011 | Haveri | A61B 8/4483 165/104.19 |
| 8,240,978 B2 * | 8/2012 | Guitton | G05D 23/1909 415/14 |
| 2003/0158482 A1 * | 8/2003 | Poland | G01H 1/00 600/446 |

(Continued)

FOREIGN PATENT DOCUMENTS

| | | |
|---|---|---|
| JP | 2005-337910 A | 12/2005 |
| KR | 10-0850268 B1 | 8/2008 |
| KR | 10-1116950 B1 | 3/2012 |

*Primary Examiner* — Helen Kwok
(74) *Attorney, Agent, or Firm* — Sughrue Mion, PLLC

(57) ABSTRACT

A portable ultrasonic probe includes a main body including a transducer to generate an ultrasonic wave and a folder portion including a display portion and pivotally coupled to an end portion of the main body, the main body includes a first heat radiation module configured to absorb and emit heat generated by the transducer, and the folder portion includes a second heat radiation module thermally coupled to the first heat radiation module when the folder portion is in a first position and configured to emit heat transmitted from the first heat radiation module.

18 Claims, 12 Drawing Sheets

(56) References Cited

U.S. PATENT DOCUMENTS

| | | | |
|---|---|---|---|
| 2005/0251035 A1* | 11/2005 | Wong | A61B 8/00 600/437 |
| 2006/0100513 A1* | 5/2006 | Hashimoto | A61B 8/00 600/437 |
| 2008/0064955 A1* | 3/2008 | Miyajima | A61B 8/00 600/437 |
| 2008/0139945 A1* | 6/2008 | Hu | A61B 8/00 600/459 |
| 2009/0043204 A1 | 2/2009 | Pelissier et al. | |
| 2010/0277305 A1* | 11/2010 | Garner | A61B 8/00 340/539.1 |
| 2010/0331702 A1* | 12/2010 | Hongou | A61B 8/14 600/459 |
| 2011/0230767 A1* | 9/2011 | Miyajima | A61B 8/00 600/459 |
| 2011/0282211 A1* | 11/2011 | Shikata | A61B 8/546 600/459 |
| 2012/0060610 A1* | 3/2012 | Oaks | A61B 8/4444 73/632 |
| 2012/0238873 A1* | 9/2012 | Lacoste | A61B 8/4461 600/439 |
| 2012/0238880 A1* | 9/2012 | Davidsen | B06B 1/0629 600/459 |
| 2013/0286593 A1* | 10/2013 | Cho | B06B 1/0292 361/707 |
| 2014/0364741 A1* | 12/2014 | Cho | A61B 8/4427 600/459 |
| 2015/0087988 A1* | 3/2015 | Lee | A61B 8/4494 600/459 |

* cited by examiner

PORTABLE ULTRASONIC PROBE

CROSS-REFERENCE TO RELATED APPLICATION

This application claims priority from Korean Patent Application No. 10-2013-0066432, filed on Jun. 11, 2013, in the Korean Intellectual Property Office, the disclosure of which is incorporated herein by reference in its entirety.

BACKGROUND

1. Field

Apparatuses and methods consistent with exemplary embodiments relate to an ultrasonic probe of an ultrasonic diagnostic apparatus to diagnose diseases.

2. Description of the Related Art

An ultrasonic diagnostic apparatus is an apparatus which projects ultrasonic waves from a surface of an object toward a target part inside the object and receives an ultrasonic echo signal reflected therefrom to noninvasively obtain a monolayer of soft tissue or an image related to a blood stream.

The ultrasonic diagnostic apparatus may be smaller, cheaper, and display a diagnostic image in real time, compared to other imaging diagnostic devices such as an X-ray device, a computerized tomography (CT) scanner, and a nuclear medicine diagnostic device. In addition, since the ultrasonic diagnostic apparatus does not cause radiation exposure, the ultrasonic diagnostic apparatus may be inherently safer. Accordingly, the ultrasonic diagnostic apparatus is widely utilized for cardiac, abdominal, and urologic diagnosis as well as maternity diagnosis.

The ultrasonic diagnostic apparatus include an ultrasonic probe which projects ultrasonic waves onto an object and receives ultrasonic echo signals reflected from the object to image the interior of the object.

SUMMARY

One or more exemplary embodiments provide a portable ultrasonic probe capable of performing imaging and displaying an imaged image to be easily identifiable. In addition, one or more exemplary embodiments provide an ultrasonic probe having a structure capable of dissipating heat generated by the ultrasonic probe.

In accordance with an aspect of an exemplary embodiment, a portable ultrasonic probe includes a main body including a transducer to generate an ultrasonic wave, and a folder portion including a display portion and pivotally coupled to an end portion of the main body, wherein the main body includes a first heat radiation module configured to absorb and emit heat generated by the transducer, and the folder portion includes a second heat radiation module thermally coupled to the first heat radiation module when the folder portion is in a first position and configured to emit heat transmitted from the first heat radiation module.

In accordance with an aspect of another exemplary embodiment, a portable ultrasonic probe includes a main body including a transducer to generate an ultrasonic wave and a first heat radiation module to absorb and emit heat generated by the transducer, and a folder portion including a display portion and a second heat radiation module thermally coupled to the first heat radiation module when the folder portion is in a first position and configured to emit heat from the first heat radiation module, wherein the main body is provided such that a surface of the main body from which the ultrasonic wave is projected is slanted with respect to an opposite surface of the surface.

In accordance with an aspect of still another exemplary embodiment, a portable ultrasonic probe includes a main body including at least one ultrasonic element configured to generate an ultrasonic wave; a foldable part movable between a first position and a second position relative to the main body; and a hinge part configured to operatively connect the foldable part to the main body, wherein the hinge part is thermally coupled to the at least one ultrasonic element of the main body.

BRIEF DESCRIPTION OF THE DRAWINGS

These and/or other aspects will become apparent and more readily appreciated from the following description of exemplary embodiments, taken in conjunction with the accompanying drawings in which.

DETAILED DESCRIPTION

Figure 1:
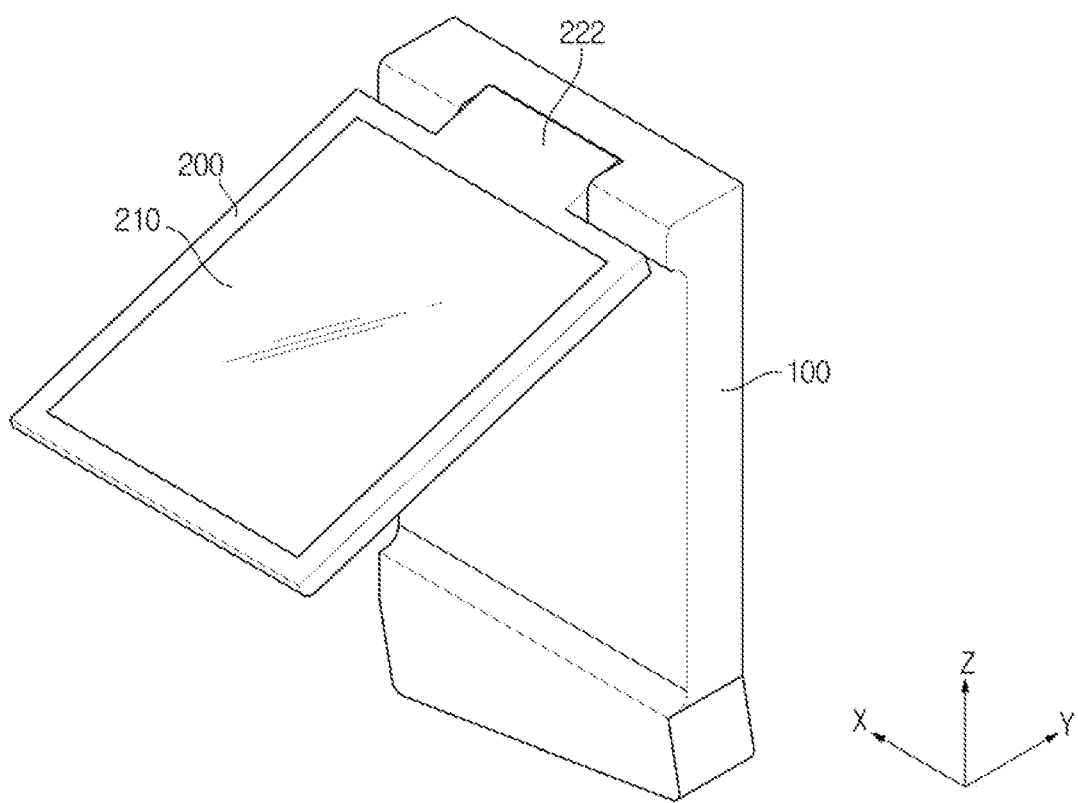
FIG. 1 is a perspective view illustrating an external appearance of a portable ultrasonic probe according to an exemplary embodiment.

Hereinafter, exemplary embodiments will now be described more fully with reference to the accompanying drawings. The exemplary embodiments may, however, be embodied in many different forms and should not be construed as being limited to the embodiments set forth herein; rather, these embodiments are provided so that this disclosure will be thorough and complete, and will fully convey the scope of the disclosure to those skilled in the art. For example, configuring elements that are singular forms may be executed in a distributed fashion, and also, configuring elements that are distributed may be combined and then executed. In the following description, well-known functions or constructions are not described in detail since they would obscure the disclosure with unnecessary detail. Also, throughout the specification, like reference numerals in the drawings denote like elements.

Figure 2:
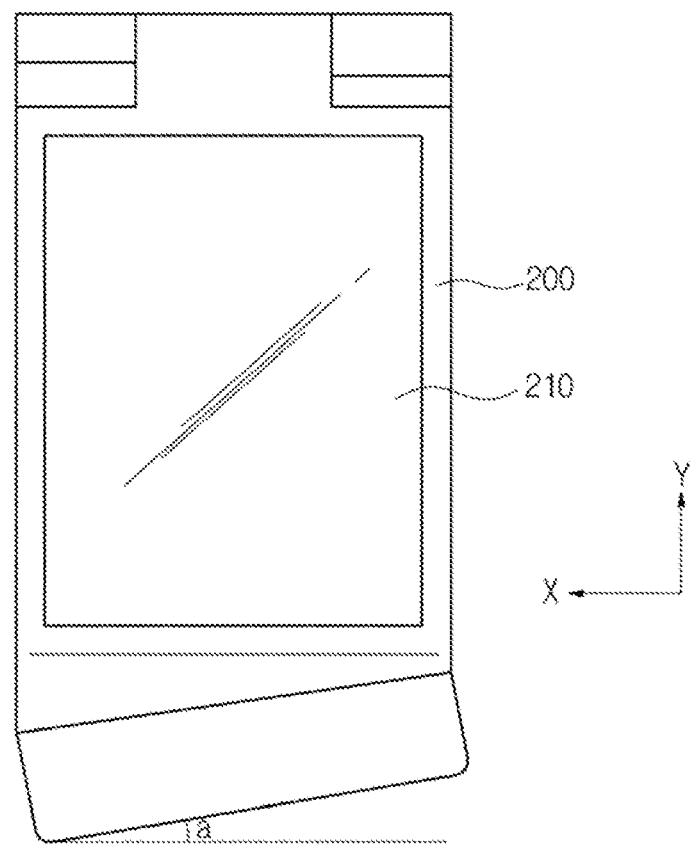
FIG. 2 is a front view illustrating a portable ultrasonic probe according to an exemplary embodiment.
Figure 3:
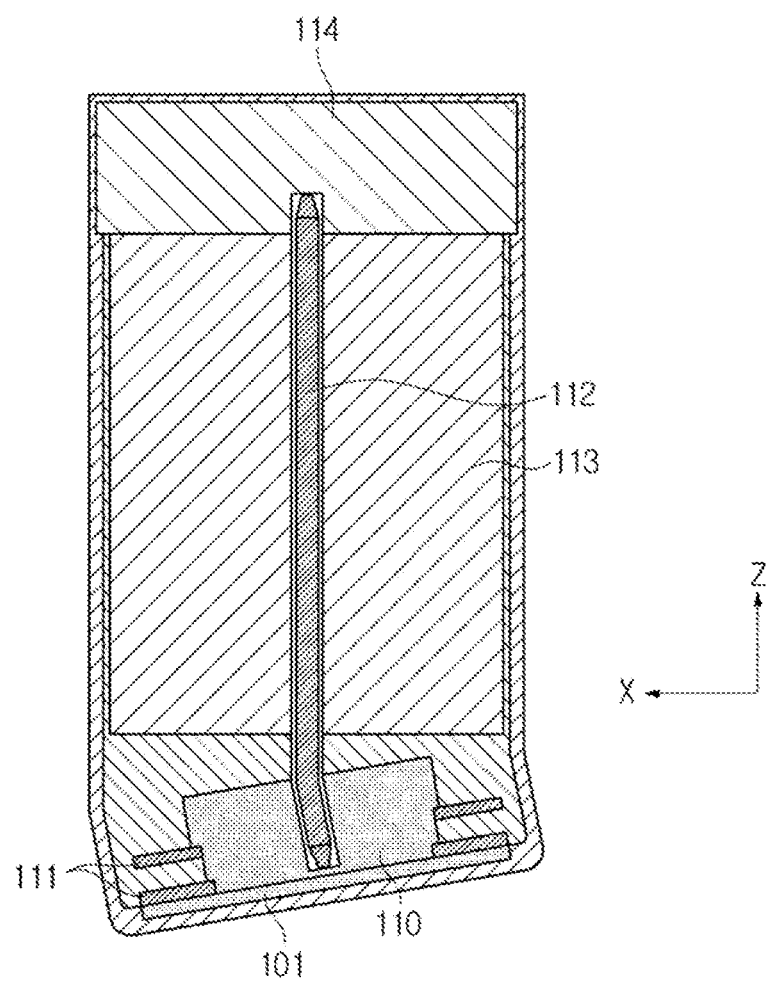
FIG. 3 is a view illustrating an inner structure for heat radiation of a main body in a portable ultrasonic probe according to an exemplary embodiment.
Figure 4:
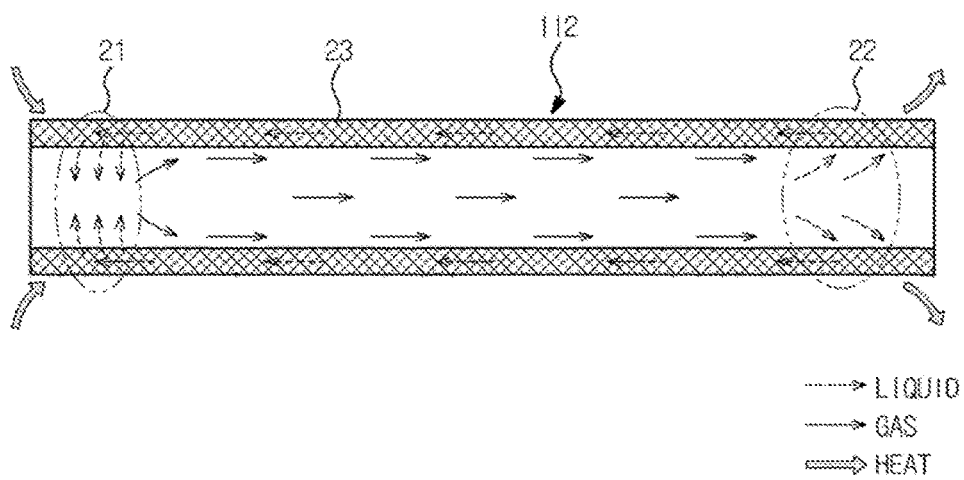
FIG. 4 is a view illustrating an operation principle of a heat pipe according to an exemplary embodiment.
Figure 5:
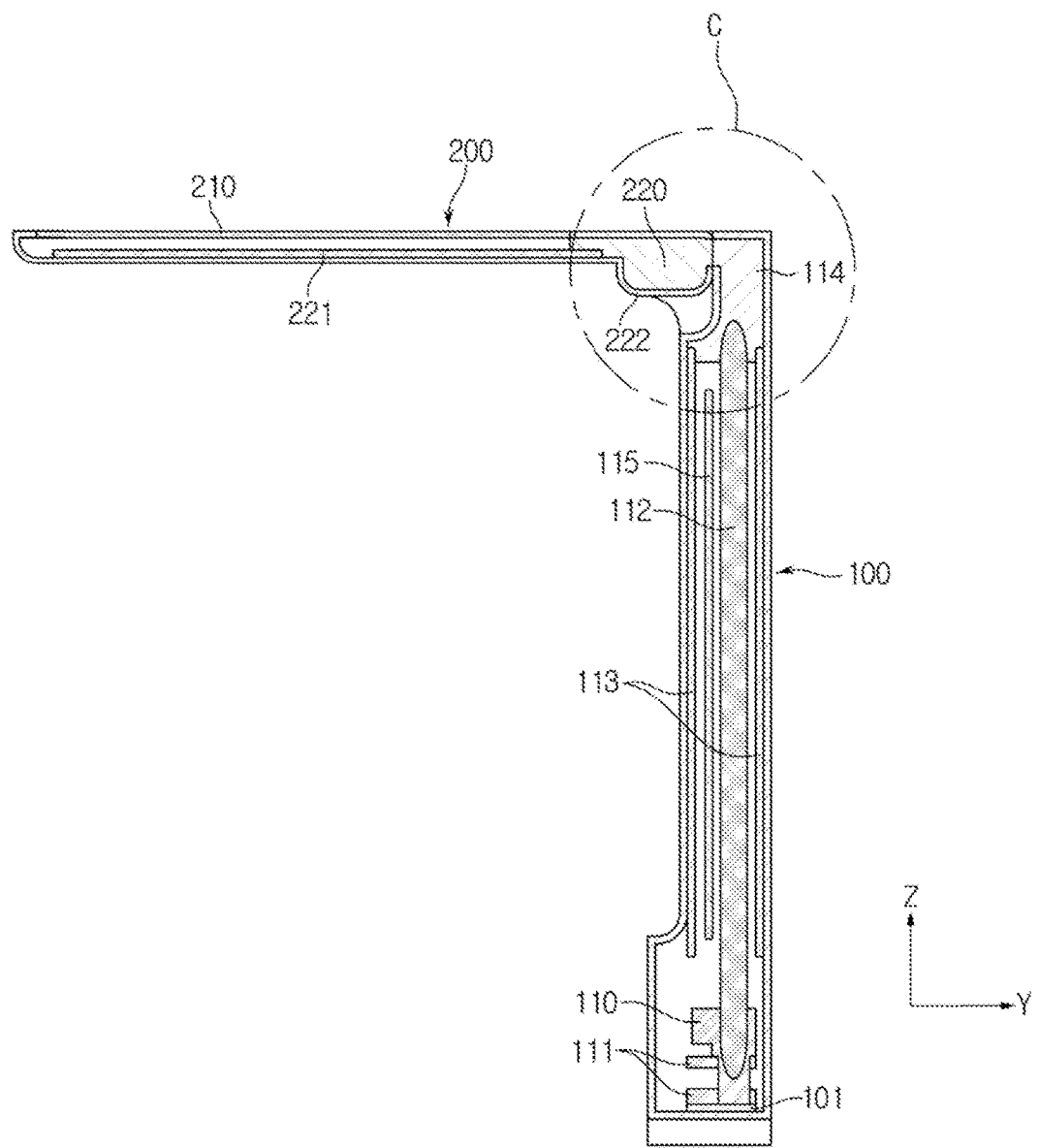
FIG. 5 is a cross-sectional view of a portable ultrasonic probe according to an exemplary embodiment.
Figure 6:
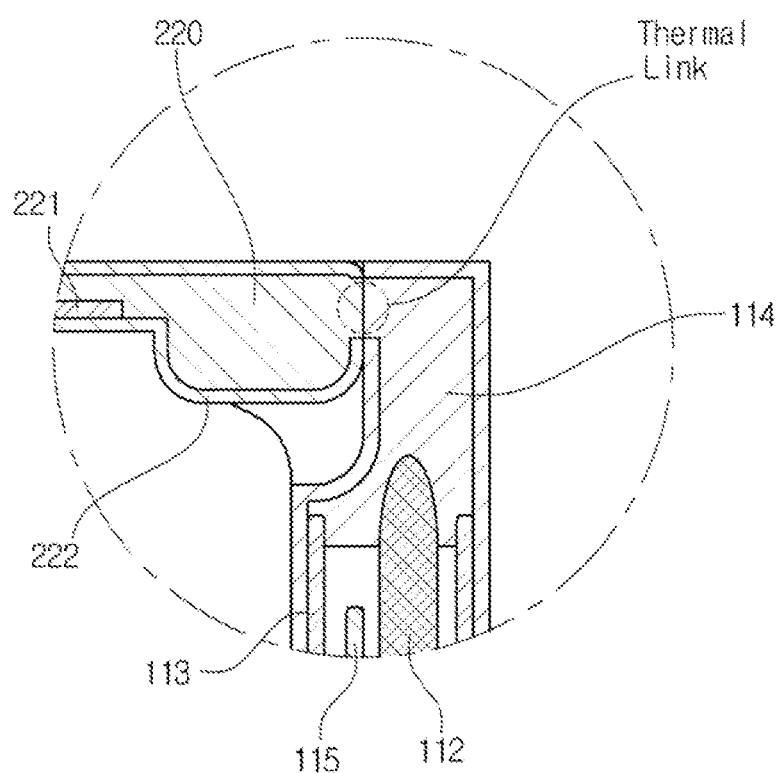
FIG. 6 is an enlarged view of region "C" in FIG. 5.
Figure 7:
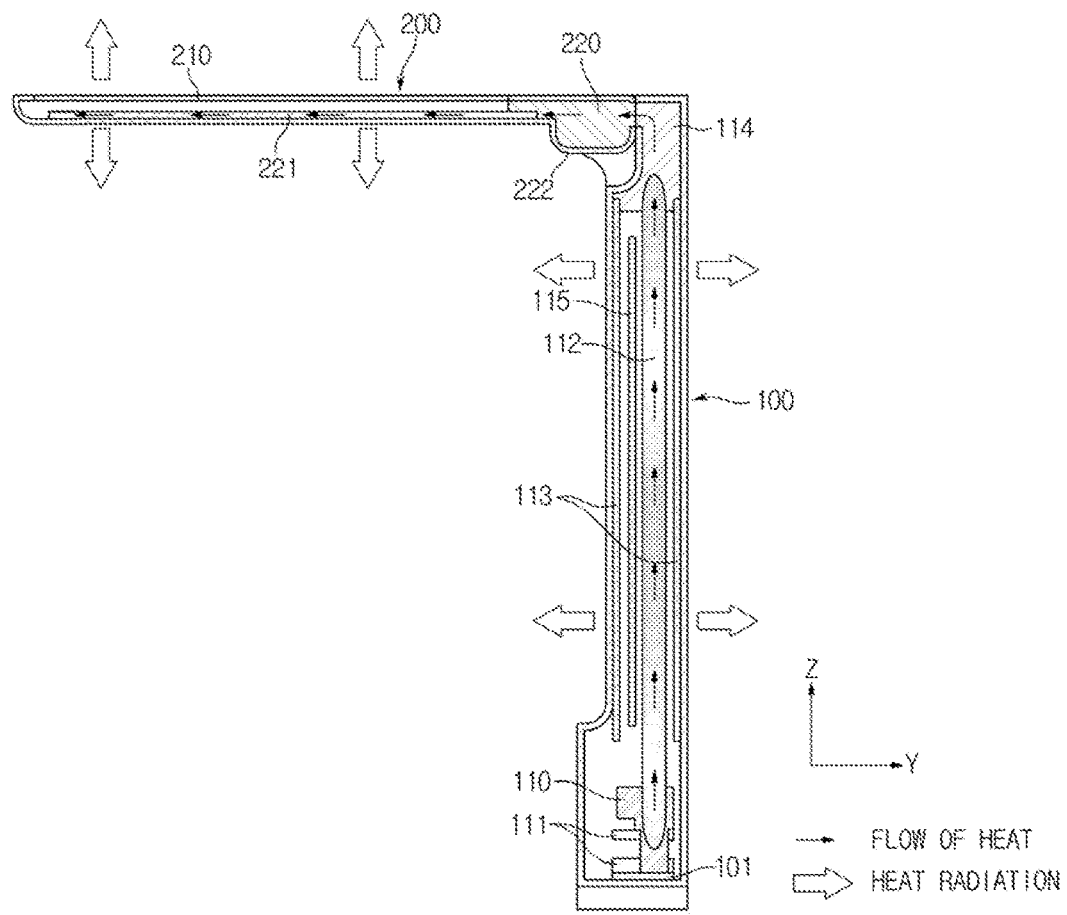
FIG. 7 is a view illustrating flow of heat in a portable ultrasonic probe according to an exemplary embodiment.

FIG. 1 is a perspective view illustrating an external appearance of a portable ultrasonic probe according to an exemplary embodiment. FIG. 2 is a front view illustrating a portable ultrasonic probe according to an exemplary embodiment. FIG. 3 is a view illustrating an inner structure for heat radiation of a main body in a portable ultrasonic probe according to an exemplary embodiment. FIG. 4 is a view illustrating an operation principle of a heat pipe according to an exemplary embodiment. FIG. 5 is a cross-sectional view of a portable ultrasonic probe according to an exemplary embodiment. FIG. 6 is an enlarged view of region "C" in FIG. 5. FIG. 7 is a view illustrating flow of heat in FIG. 5.

Referring to FIG. 1, the portable ultrasonic probe includes a main body 100 having a transducer 101 to generate ultrasonic waves, and a folder portion 200 pivotally coupled to the main body 100 and having a display portion 210 on which an ultrasonic image is displayed.

The main body 100 includes a transducer 101 to generate ultrasonic waves and a first heat radiation module which absorbs and emits heat generated by the transducer 101.

In an exemplary embodiment of the transducer 101, a magnetostrictive ultrasonic transducer using a magnetostrictive effect of a magnetic substance, a piezoelectric ultrasonic transducer using a piezoelectric effect of a piezoelectric substance, or the like may be utilized as the ultrasonic transducer 101. In addition, a capacitive micromachined ultrasonic transducer (hereinafter, referred to as a "cMUT") which transmits and receives ultrasonic waves using vibrations of several hundreds or thousands of micromachined thin films may also be utilized as the ultrasonic transducer 101. Herein, for illustrative purposes, the cMUT will be described as an example of the transducer 101.

Referring to FIG. 2, a surface from which ultrasonic waves are projected from the transducer 101 included in the main body 100 has a predetermined angle (a) with an X-axis. That is, an ultrasonic projection surface is not parallel with an opposite surface (e.g., a top surface) of the main body 100, and is provided to be slanted with respect to the opposite surface.

In a case in which the ultrasonic projection surface is provided as shown in FIG. 2, a user may easily view an image displayed on the display portion 210 of the folder portion 200 when the folder portion 200 is opened. That is, when the slanted ultrasonic projection surface comes into contact with an inspection part of an object, the display portion 210 of the folder portion 200 is tilted toward a user to the same degree as the ultrasonic projection surface is slanted. As a result, a user may easily identify an image displayed on the display portion 210 without shifting the user's position or tilting the ultrasonic probe to view the display portion 210 while checking the inspection part.

The first heat radiation module which absorbs and emits heat generated by the transducer 101 includes a heat spreader 110 to absorb heat generated by the transducer 101, a heat pipe 112 installed to the heat spreader 110 to transfer heat absorbed by the heat spreader 110 in a direction opposite to a direction in which ultrasonic waves are projected, and a first connection portion 114 which is installed to come into thermal contact with a condensation portion 22 of the heat pipe 112 and absorbs heat transferred from the heat pipe 112.

The heat spreader 110 is installed on a surface of the transducer 101 to absorb heat generated by the transducer 101. The heat spreader 110 may comprise a metal such as, for example, aluminum.

The heat spreader 110 comes into thermal contact with the transducer 101 to absorb heat generated by the transducer 101. FIG. 3 shows a structure of the heat spreader 110 in a case in which the cMUT is used as an example of the transducer 101. In general, a cMUT array is bonded to an integrated circuit such as an application specific integrated circuit (ASIC) in a flip chip bonding manner, and signal lines of the ASIC to which the cMUT array is bonded may be bonded onto a printed circuit board 111 in a wire bonding manner. FIG. 3 shows a state in which the heat spreader 110 is installed on the printed circuit board 111. The heat spreader 110 may be installed by being inserted into the printed circuit board 111 to come into thermal contact with the transducer 101.

Thus, the heat spreader 110 may be provided such that the heat spreader 110 comes into direct contact with the transducer 101. Alternatively, the heat spreader 110 may be provided such that a predetermined gap is defined between the heat spreader 110 and the transducer 101 without direct contact therebetween. The gap between the heat spreader 110 and the transducer 101 may be filled with thermal grease or a phase change material which is a thermal medium having a thermal conductivity. Heat generated by the transducer 101 may be directly transferred through the heat spreader 110, or transferred to the heat spreader 110 through the thermal grease or the phase change material filled in the gap.

The heat spreader 110 may be provided with the heat pipe 112 to transfer heat absorbed by the heat spreader 110 in a direction opposite to a direction in which ultrasonic waves are projected, namely, in a Z-axis direction. As shown in FIG. 3, the heat pipe 112 may be installed in a shape bent with respect to the Z-axis direction to substantially the same degree as the ultrasonic projection surface is slanted with respect to an X-axis direction.

The heat spreader 110 may be provided with an insertion groove, and the heat pipe 112 may be inserted into the insertion groove to be installed to the heat spreader 110. To efficiently transfer heat from the heat spreader 110 to the heat pipe 112, the insertion groove provided in the heat spreader 110 may have a depth sufficient to substantially reach a thermal contact surface between the heat spreader 110 and the transducer 101. In other words, the heat pipe 112 may be inserted to the heat spreader 110 to substantially reach the thermal contact surface between the heat spreader 110 and the transducer 101.

FIG. 4 is a view illustrating an operation principle of the heat pipe 112 according to an exemplary embodiment.

The heat pipe 112 is a device, evacuated to a vacuum state, in which a working fluid is injected into a closed pipe-shaped container thereof.

The working fluid in the heat pipe 112 change a phase thereof to transfer heat, which will be described below.

Referring to FIG. 4, when heat is applied to an evaporation portion 21 of the heat pipe 112, the heat is transferred into the heat pipe 112 by a thermal conductivity via an outer wall thereof.

Since the inside of the heat pipe 112 has higher pressure, evaporation of the working fluid may occur even at low temperature on a surface of a wick 23 of the heat pipe 112.

Gas density and pressure are increased in the evaporation portion 21 due to the evaporation of the working fluid, and thus a pressure gradient is provided in a gas passage of a central portion of the heat pipe 112 in a direction toward a condensation portion 22 having relatively low density and pressure of gas. Accordingly, gas is moved in the direction toward the condensation portion 22.

In this case, the gas is moved with an amount of heat equal to or greater than that of evaporative latent heat.

The gas moved to the condensation portion 22 dissipates heat while condensing on an inner wall of the condensation portion 22 having a relatively low temperature, and returns back to a liquid phase.

The working fluid returned to the liquid phase is again moved toward the evaporation portion 21 through pores within the wick 23 by capillary pressure or gravity of the wick 23.

Through the above described processes, heat transfer may be performed.

The evaporation portion 21 of the heat pipe 112 is installed to come into thermal contact with the heat spreader 110 to absorb heat generated by the transducer 101, and the heat pipe 112 transfers the heat generated by the transducer 101 in the Z-axis direction according to the above-mentioned heat transfer process.

The condensation portion 22 of the heat pipe 112 is installed to come into thermal contact with the first connection portion 114, and transfers heat to the first connection portion 114. As shown in FIG. 3, the condensation portion 22 of the heat pipe 112 may be installed to the first connection portion 114 by being inserted thereinto.

The first connection portion 114 may comprise a metal such as aluminum having a higher thermal conductivity. Referring to FIG. 5, the first connection portion 114 is installed at an end portion of the main body 100 which is located in a direction opposite to a direction in which ultrasonic waves are projected. The first connection portion 114 comes into thermal contact with the condensation portion 22 of the heat pipe 112 to absorb heat transferred from the heat pipe 112. In addition, when the portable ultrasonic probe is opened by pivoting the folder portion 200, the first connection portion 114 comes into contact with a second connection portion 220 of a second heat radiation module included in the folder portion 200 to transfer heat to the second connection portion 220.

As shown in FIGS. 3 and 5, the first heat radiation module may further include heat radiation plates 113 provided to emit heat generated by other components of the main body 100, which may include the transducer 101, a board 115 to output signals for driving the transducer 101, and the like, via a housing of the main body 100 to the outside.

As shown in FIG. 5, the heat radiation plates 113 may be installed on an inner side of a first surface of the main body 100, which comes into contact with the folder portion 200 when the portable ultrasonic probe is folded, and on an inner side of a second surface opposite to the first surface, respectively. Since the heat radiation plates 113 are installed on the inner sides of the first and second surfaces having a wider surface area, heat absorbed by the heat radiation plates 113 may be dissipated more efficiently.

As shown in FIG. 5, the heat radiation plates 113 are also installed to the first connection portion 114, and may transfer heat absorbed by the heat radiation plates 113 to the first connection portion 114.

Although it is shown in the drawings that the heat radiation plates 113 do not come into direct contact with the heat spreader 110, exemplary embodiments are not limited thereto. For example, the heat radiation plates 113 may also be installed to come into direct contact with the heat spreader 110 to dissipate heat absorbed by the heat spreader 110.

In addition, the heat radiation plates 113 may include a Peltier element, or a heat radiation member including a Peltier element may be additionally or alternatively installed to the heat radiation plate 113. Consequently, heat radiation efficiency may be improved.

Referring to FIG. 7, heat generated by the transducer 101 is absorbed by the heat spreader 110, and the heat absorbed by the heat spreader 110 is transferred to the first connection portion 114 through the heat pipe 112 installed to the heat spreader 110. The heat transferred from the heat pipe 112 to the first connection portion 114 is transferred to the second connection portion 220 by contact between the first and second connection portions 114 and 220 when the portable ultrasonic probe is opened. Heat generated by other components of the main body 100, which may include the transducer 101, the board 115 to output signals for driving the transducer 101, and the like, is absorbed by the heat radiation plates 113, and is emitted via the housing of the main body 100 to the outside. The heat transferred to the second connection portion 220 is emitted to the outside through a heat radiation plate 221 connected to the second connection portion 220.

The folder portion 200 includes the display portion 210 to display an ultrasonic image and the second heat radiation module which absorbs and emits heat transferred from the first heat radiation module.

As shown in FIG. 1, the display portion 210 is provided on a first surface of the folder portion 200 opposite to a second surface thereof which comes into contact with the main body 100 when the folder portion 200 is folded.

A user may identify an ultrasonic image displayed on the display portion 210 while checking an object in a state in which the portable ultrasonic probe is opened by pivoting the folder portion 200 as shown in FIG. 1.

Since the ultrasonic projection surface of the main body 100 is slanted as shown in FIG. 2, the display portion 210 is directed toward a user when the portable ultrasonic probe is changed to a state as shown in FIG. 1 by opening thereof. Accordingly, a user may not need to shift the user's position or tilt the portable ultrasonic probe to view the display portion 210.

The second heat radiation module includes the second connection portion 220 to absorb heat transferred from the first heat radiation module. FIG. 6 is an enlarged view illustrating region "C" of FIG. 5, namely, a contact region between the first and second connection portions 114 and 220. Referring to FIG. 6, the first and second connection portions 114 and 220 come into thermal contact with each other when the portable ultrasonic probe is opened. The first and second connection portions 114 and 220 may not be in contact with each other when the folder portion 200 is folded, but the first and second connection portions 114 and 220 may come into thermal contact with the each other when the portable ultrasonic probe is opened by pivoting the folder portion 200.

Similar to the first connection portion 114, the second connection portion 220 may comprise a metal such as, for example, aluminum having a higher thermal conductivity. Therefore, when the second connection portion 220 comes into contact with the first connection portion 114, the second connection portion 220 absorbs heat transferred from the heat pipe 112 of the first connection portion 114.

The first and second connection portions 114 and 220 may also be provided such that a predetermined gap is defined between the first and second connection portions 114 and 220 without direct contact between first and second connection portions 114 and 220 when the portable ultrasonic probe is opened. The gap may be filled with thermal grease or a phase change material which is a thermal medium having a thermal conductivity. In this case, heat of the first connection portion 114 is transferred to the second connection portion 220 through the above-mentioned thermal medium.

The second heat radiation module may include the heat radiation plate 221 to absorb and emit heat transferred from the second connection portion 220. As shown in FIG. 7, the heat radiation plate 221 may be installed on an inner side of a surface of the folder portion 200 which comes into contact with the main body 100 when the portable ultrasonic probe is folded. Thus, the heat radiation plate 221 is installed on the inner side of the surface having a wider surface area, heat absorbed by the heat radiation plate 221 may be more efficiently dissipated. Although not shown, the second heat radiation module may also include a heat pipe. The heat pipe may be installed to the second connection portion 220 to absorb heat from the second connection portion 220 and transfer the absorbed heat to an opposite side of the folder portion 200. In addition, it may be possible to dissipate heat transferred from the heat pipe by installing a heat radiation member to the condensation portion 22 of the heat pipe.

The folder portion 200 may include a coupling portion 222 which couples the folder portion 200 and the main body 100 such that the folder portion 200 is pivotally coupled to the main body 100.

The folder portion 200 may be hinge-coupled to the main body 100 by the coupling portion 222, and the coupling portion 222 may have a rotation shaft provided parallel with the X-axis such that the folder portion 200 is pivoted as shown in FIG. 1. Although it is shown in FIG. 1 that the coupling portion 222 has one rotation shaft axis, a coupling portion 230 (see FIG. 12) may have two rotation shaft axes perpendicular to each other, e.g., a first rotation shaft axis parallel with the Y-axis and a second rotation shaft axis parallel with a plane perpendicular to the first rotation shaft.

Figure 12:
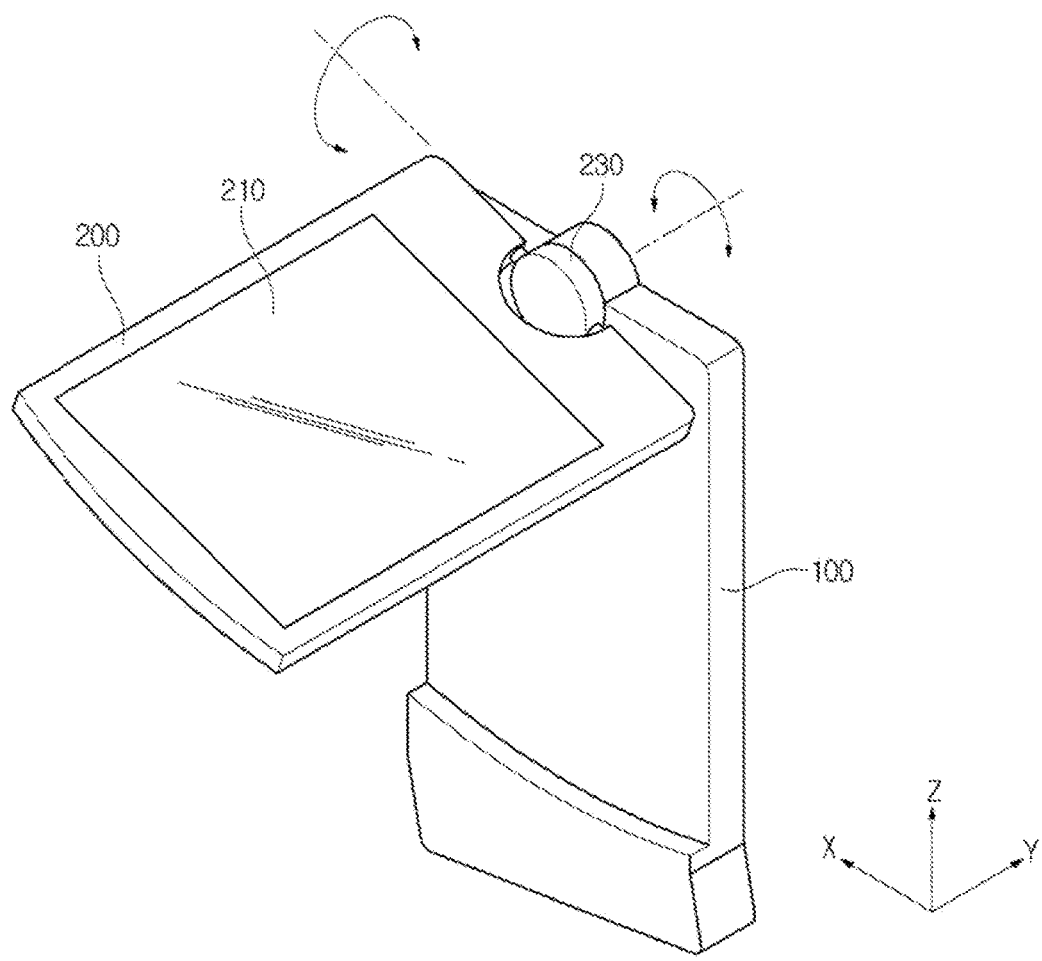
FIG. 12 is a perspective view illustrating an external appearance of a portable ultrasonic probe according to a still another exemplary embodiment.

When the coupling portion 230 has the first and second rotation shafts, the folder portion 200 may be rotated as shown in FIG. 12. Accordingly, a user may identify an image displayed on the display portion 210 more easily by rotating the folder portion 200 to a desired position.

Figure 8:
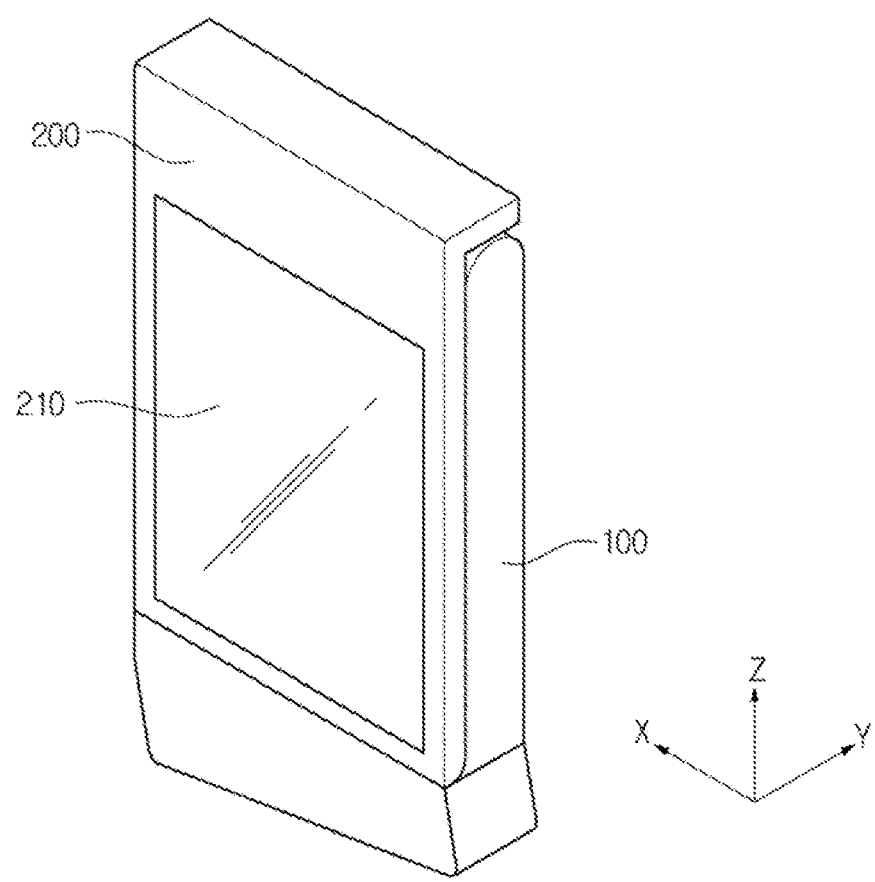
FIGS. 8 and 9 are perspective views illustrating an external appearance of a portable ultrasonic probe according to another exemplary embodiment.
Figure 9:
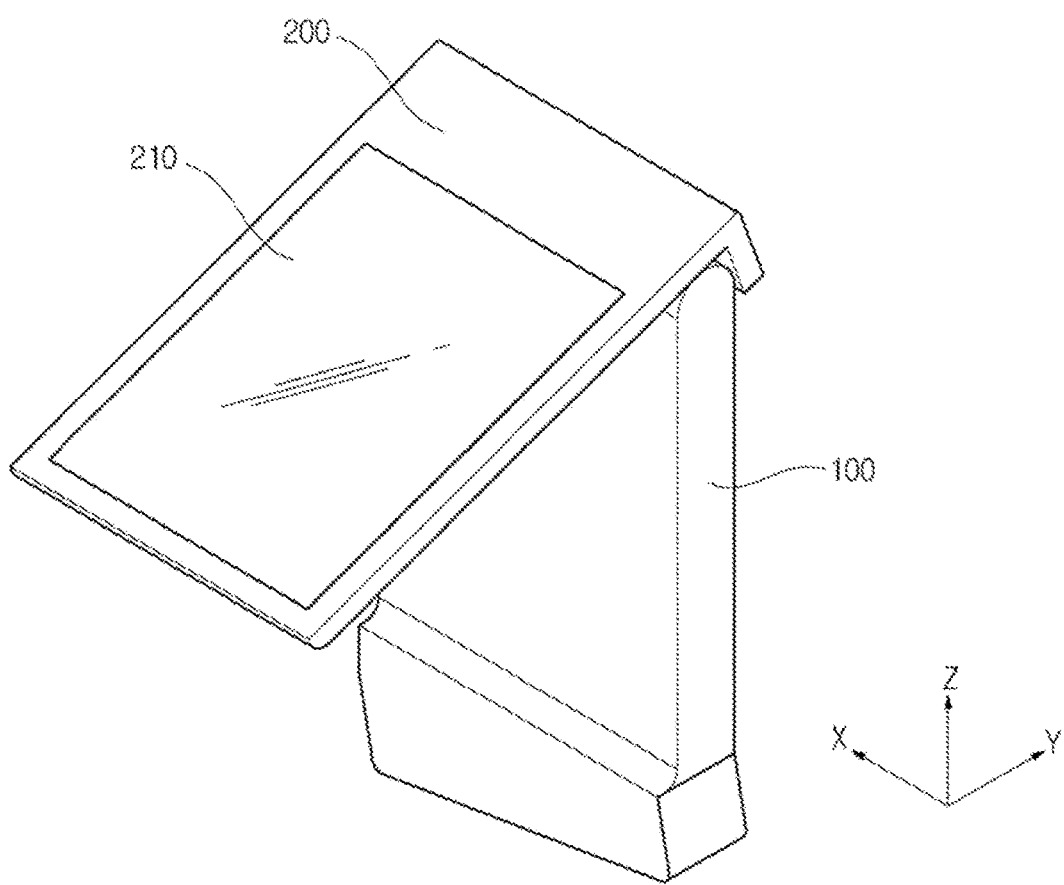
Figure 10:
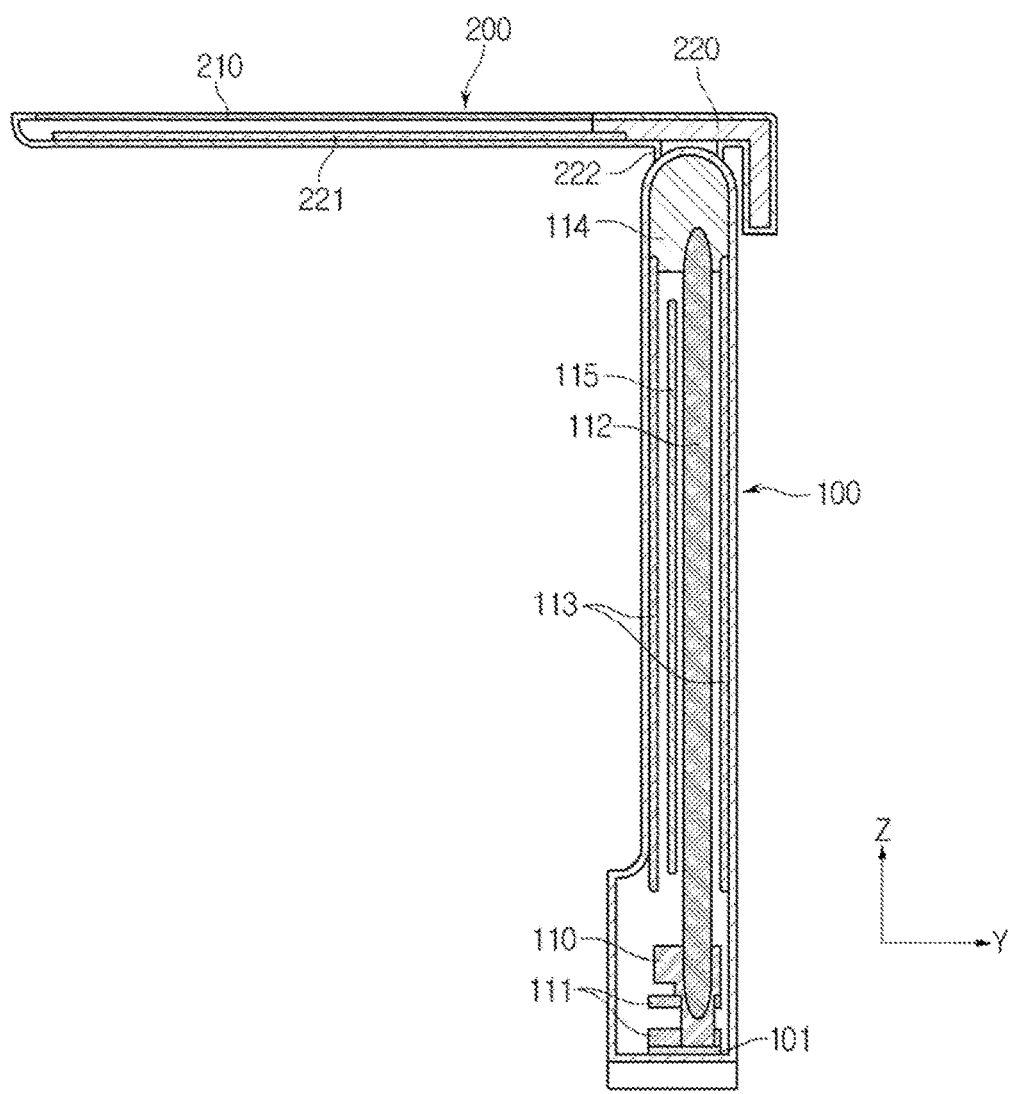
FIG. 10 is a cross-sectional view of a portable ultrasonic probe according to another exemplary embodiment.
Figure 11:
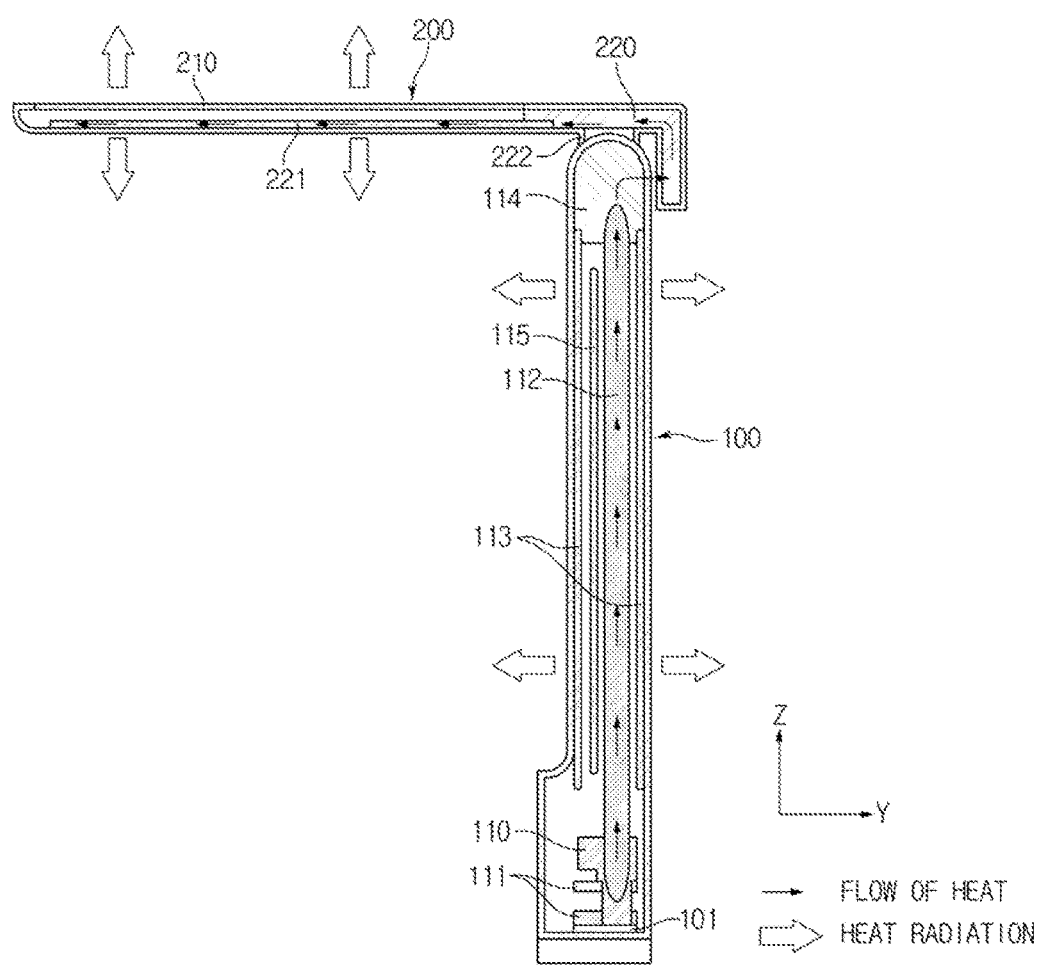
FIG. 11 is a view illustrating flow of heat in a portable ultrasonic probe according to another exemplary embodiment.

FIGS. 8 and 9 are perspective views illustrating an external appearance of a portable ultrasonic probe according to another exemplary embodiment. FIG. 10 is a cross-sectional view of a portable ultrasonic probe according to another exemplary embodiment. FIG. 11 is a view illustrating flow of heat in FIG. 10.

Referring to FIGS. 8 and 9, the portable ultrasonic probe includes a main body 100 having a transducer 101 to generate ultrasonic waves, and a folder portion 200 pivotally coupled to the main body 100 and having a display portion 210 on which an ultrasonic image is displayed.

The main body 100 includes the transducer 101 to generate ultrasonic waves and a first heat radiation module which absorbs and emits heat generated by the transducer 101.

In the ultrasonic probe shown in FIGS. 8 to 11, a surface onto which ultrasonic waves are projected from the transducer 101 included in the main body 100 may have a predetermined angle (a) with the X-axis, as shown in FIG. 2. That is, the ultrasonic projection surface is not parallel with an opposite surface (e.g., a top surface) of the main body 100, and is provided to be slanted with respect to the opposite surface.

In a case in which the ultrasonic projection surface is provided as shown in FIG. 2, a user may easily view the display portion 210 of the folder portion 200 when the folder portion 200 is opened. That is, when the slanted ultrasonic projection surface comes into contact with an inspection part of an object, the display portion 210 of the folder portion 200 is tilted toward a user to the same degree as the ultrasonic projection surface is slanted. As a result, a user may easily identify an image displayed on the display portion 210 without shifting the user's position or tilting the ultrasonic probe to view the display portion 210 while checking the inspection part.

The first heat radiation module which absorbs and emits heat generated by the transducer 101 includes a heat spreader 110 to absorb heat generated by the transducer 101, a heat pipe 112 installed to the heat spreader 110 to transfer heat absorbed by the heat spreader 140 in a direction opposite to a direction in which ultrasonic waves are projected, and a first connection portion 114 which is installed to come into thermal contact with a condensation portion 22 (see FIG. 4) of the heat pipe 112 and absorbs heat transferred from the heat pipe 112.

The heat spreader 110 is installed on a surface of the transducer 101 to absorb heat generated by the transducer 101. The heat spreader 110 may comprise a metal such as aluminum.

The heat spreader 110 comes into thermal contact with the transducer 101 to absorb heat generated by the transducer 101. FIGS. 10 and 11 show a structure of the heat spreader 110 in a case in which a cMUT is used as an example of the transducer 101. In general, the cMUT array is bonded to an integrated circuit such as an application specific integrated circuit (ASIC) in a flip chip bonding manner, and signal lines of the ASIC to which the cMUT array is bonded may be bonded onto a printed circuit board 111 in a wire bonding manner. FIGS. 10 and 11 show a state in which the heat spreader 110 is installed on the printed circuit board 111. The heat spreader 110 is installed by being inserted into the printed circuit board 111 to come into thermal contact with the transducer 101.

The heat spreader 110 may be provided such that the heat spreader 110 comes into direct contact with the transducer 101 or a predetermined gap is defined between the heat spreader 110 and the transducer 101 without direct contact therebetween. The gap between the heat spreader 110 and the transducer 101 may be filled with thermal grease or a phase change material which is a thermal medium having a thermal conductivity. Heat generated by the transducer 101 is directly transferred through the heat spreader 110, or transferred to the heat spreader 110 through the thermal grease or the phase change material filled in the gap.

The heat spreader 110 may be provided with the heat pipe 112 to transfer heat absorbed by the heat spreader 110 in a direction opposite to a direction in which ultrasonic waves are projected, namely, in a Z-axis direction. As shown in FIG. 3, the heat pipe 112 may be installed in a shape bent with respect to the Z-axis direction to substantially the same degree as the ultrasonic projection surface is slanted with respect to the X-axis direction.

The heat spreader 110 may be provided with an insertion groove, and the heat pipe 112 may be inserted into the insertion groove to be installed to the heat spreader 110. To efficiently transfer heat from the heat spreader 110 to the heat pipe 112, the insertion groove provided in the heat spreader 110 may have a depth sufficient to substantially reach a thermal contact surface between the heat spreader 110 and the transducer 101. In other words, the heat pipe 112 may be inserted to as the heat spreader 110 to substantially reach the thermal contact surface between the heat spreader 110 and the transducer 101.

An evaporation portion 21 (see FIG. 4) of the heat pipe 112 is installed to come into thermal contact with the heat spreader 110 to absorb heat generated by the transducer 101, and the heat pipe 112 transfers the heat generated by the transducer 101 in the Z-axis direction.

The condensation portion 22 of the heat pipe 112 is installed to come into thermal contact with the first connection portion 114, and transfers heat to the first connection portion 114. As shown in FIGS. 10 and 11, the condensation portion 22 of the heat pipe 112 may be installed to the first connection portion 114 by being inserted thereinto.

The first connection portion 114 may comprise metal such as, for example, aluminum having a higher thermal conductivity. Referring to FIGS. 10 and 11, the first connection portion 114 is installed at an end portion of the main body 100 which is located in a direction opposite to a direction in which ultrasonic waves are projected. The first connection portion 114 comes into thermal contact with the condensation portion 22 of the heat pipe 112 to absorb heat transferred from the heat pipe 112. In addition, when the portable ultrasonic probe is opened by pivoting the folder portion 200, the first connection portion 114 comes into contact with a second connection portion 220 of a second heat radiation module included in the folder portion 200 to transfer heat to the second connection portion 220.

As shown in FIGS. 10 and 11, the first heat radiation module may further include heat radiation plates 113 provided to emit heat generated by other components of the main body 100, which may include the transducer 101, a board 115 to output signals for driving the transducer 101, and the like, via a housing of the main body 100 to the outside.

As shown in FIGS. 10 and 11, the heat radiation plates 113 may be installed on an inner side of a first surface of the main body 100, which comes into contact with the folder portion 200 when the portable ultrasonic probe is folded, and on an inner side of a second surface opposite to the first surface, respectively. Since the heat radiation plates 113 are installed on the first and second inner sides of the surfaces having a wider surface area, heat absorbed by the heat radiation plates 113 may be more efficiently dissipated.

As shown in FIGS. 10 and 11, the heat radiation plates 113 are installed to the first connection portion 114, and may transfer heat absorbed by the heat radiation plates 113 to the first connection portion 114.

Although it is shown in the drawings that the heat radiation plates 113 do not come into direct contact with the heat spreader 110, exemplary embodiments are not limited thereto. For example, the heat radiation plates 113 may also be installed to come into direct contact with the heat spreader 110 to dissipate heat absorbed by the heat spreader 110.

In addition, the heat radiation plates 113 may include a Peltier element, or a heat radiation member including a Peltier element may be additionally or alternatively installed to the heat radiation plate 113. Consequently, heat radiation efficiency may be improved.

Referring to FIG. 11, heat generated by the transducer 101 is absorbed into the heat spreader 110, and heat absorbed by the heat spreader 110 is transferred to the first connection portion 114 through the heat pipe 112 installed to the heat spreader 110. The heat transferred from the heat pipe 112 to the first connection portion 114 is transferred to the second connection portion 220 by contact between the first and second connection portions 114 and 220 when the portable ultrasonic probe is opened. Heat generated by other components of the main body 100, which may include the transducer 101, a board 115 to output signals for driving the transducer 101, and the like, is absorbed into the heat radiation plates 113, and is emitted via the housing of the main body 100 to the outside. The heat transferred to the second connection portion 220 is emitted to the outside through a heat radiation plate 221 connected to the second connection portion 220.

The folder portion 200 includes the display portion 210 to display an ultrasonic image and the second heat radiation module which absorbs and emits heat transferred from the first heat radiation module.

As shown in FIGS. 8 and 9, the display portion 210 is provided on a first surface opposite to a second surface of the folder portion 200 which comes into contact with the main body 100 when the folder portion 200 is folded.

A user may identify an ultrasonic image displayed on the display portion 210 while checking an object in a state in which the portable ultrasonic probe is opened by pivoting the folder portion 200, as shown in FIG. 9.

Since the ultrasonic projection surface of the main body 100 is slanted as shown in FIGS. 8 and 9, the display portion 210 is directed toward a user when the portable ultrasonic probe is changed to a state as shown in FIG. 9 by opening the portable ultrasonic probe. Accordingly, a user may not need to shift the user's position or tilt the portable ultrasonic probe to view the display portion 210.

The second heat radiation module includes the second connection portion 220 to absorb heat transferred from the first heat radiation module. Referring to FIGS. 10 and 11, unlike the second connection portion 220 shown in FIGS. 5 to 7, the second connection portion 220 is provided in the form of encircling the first connection portion 114. Accordingly, when the portable ultrasonic probe is opened, the second connection portion 220 is moved to a position, which may come into thermal contact with the first connection portion 114 at a surface (e.g., top surface) of the main body 100, to be supplied with heat from the first connection portion 114.

The second heat radiation module may include the heat radiation plate 221 to absorb and emit heat transferred from the second connection portion 220. As shown in FIG. 10, the heat radiation plate 221 may be installed on an inner side of a surface of the folder portion 200 which comes into contact with the main body 100 when the portable ultrasonic probe is folded. Since the heat radiation plate 221 is installed on the inner side of the surface having a wider surface area, heat absorbed by the heat radiation plate 221 may be more efficiently dissipated. Although not shown, the second heat radiation module may also include a heat pipe. The heat pipe may be installed to the second connection portion 220 to absorb heat from the second connection portion 220 and transfer the absorbed heat to an opposite side of the folder portion 200. In addition, it may be possible to dissipate heat transferred from the heat pipe by installing a heat radiation member to the condensation portion 22 of the heat pipe.

The folder portion 200 may include the coupling portion 222 (see FIG. 1) which couples the folder portion 200 and the main body 100 such that the folder portion 200 is pivotally coupled to the main body 100.

The folder portion 200 may be hinge-coupled to the main body 100 by the coupling portion 222, and the coupling portion 222 may have a rotation shaft provided parallel with the X-axis such that the folder portion 200 is pivoted as shown in FIG. 9. Although it is shown in FIG. 1 that the coupling portion 222 has one rotation shaft axis, a coupling portion 230 may also have two rotation shaft axes perpendicular to each other, e.g., a first rotation shaft axis parallel with the Y-axis and a second rotation shaft axis parallel with a plane perpendicular to the first rotation shaft axis as shown in FIG. 12.

When the coupling portion 230 has the first and second rotation shafts, the folder portion 200 may be rotated as shown in FIG. 12. Accordingly, a user may identify an image displayed on the display portion 210 more easily by rotating the folder portion 200 to a desired position.

As is apparent from the above description, it may be possible to enhance thermal stability of a portable ultrasonic probe by efficiently emitting heat generated by the portable ultrasonic probe to the outside.

Although a few exemplary embodiments have been shown and described, it would be appreciated by those skilled in the art that changes may be made in these embodiments without departing from the principles and spirit of the disclosure, the scope of which is defined in the claims and their equivalents.

What is claimed is:

1. A portable ultrasonic probe comprising:
    a main body comprising a transducer to generate an ultrasonic wave; and
    a folder portion comprising a display portion and pivotally coupled to an end portion of the main body,
    wherein the main body comprises a first heat radiation module configured to absorb and emit heat generated by the transducer,
    wherein the folder portion comprises a second heat radiation module thermally coupled to the first heat radiation module when the folder portion is in a first position and configured to emit heat transmitted from the first heat radiation module,
    wherein the folder portion further comprises a coupling portion provided at an end portion thereof such that the folder portion is pivotally coupled to an end portion of the main body by the coupling portion; and
    the coupling portion comprises at least one rotation shaft such that the folder portion is rotated around at least one rotation shaft axis of the at least one rotation shaft.

2. The portable ultrasonic probe according to claim 1, wherein the first heat radiation module comprises:
    a heat spreader provided on a first surface of the transducer to absorb the heat generated by the transducer;
    a heat pipe provided to the heat spreader to transfer the heat absorbed by the heat spreader in a direction opposite to a direction in which the ultrasonic wave is projected; and
    a first connection portion provided to the heat pipe and thermally coupled to the second heat radiation module when the folder portion is in the first position to transfer heat transferred through the heat pipe to the second heat radiation module.

3. The portable ultrasonic probe according to claim 2, wherein the first heat radiation module further comprises at least one heat radiation plate provided to the heat spreader to emit the heat absorbed by the heat spreader.

4. The portable ultrasonic probe according to claim 2, wherein the first connection portion comprises a metal.

5. The portable ultrasonic probe according to claim 2, wherein the display portion is provided on a first surface opposite to a second surface of the folder portion which comes into contact with the main body when the folder portion is folded.

6. The portable ultrasonic probe according to claim 1, wherein the second heat radiation module comprises:
    a connection portion thermally coupled to the first heat radiation module when the folder portion is in the first position; and
    a heat radiation plate connected to the connection portion to emit heat transferred from the connection portion.

7. The portable ultrasonic probe according to claim 6, wherein the second heat radiation module further comprises a heat pipe configured to transfer heat absorbed by the connection portion to the heat radiation plate.

8. The portable ultrasonic probe according to claim 1, wherein a surface of the main body from which the ultrasonic wave is projected has a predetermined angle with respect to an opposite surface of the main body.

9. A portable ultrasonic probe comprising:
    a main body comprising a transducer to generate an ultrasonic wave and a first heat radiation module to absorb and emit heat generated by the transducer; and
    a folder portion comprising a display portion and a second heat radiation module thermally coupled to the first heat radiation module when the folder portion is in a first position and configured to emit heat from the first heat radiation module,
    wherein the main body is provided such that a surface of the main body from which the ultrasonic wave is projected is slanted with respect to an opposite surface of the main body,
    wherein the folder portion further comprises a coupling portion provided at an end portion thereof such that the folder portion is pivotally coupled to an end portion of the main body by the coupling portion; and
    the coupling portion comprises at least one rotation shaft such that the folder portion is rotated around at least one rotation shaft axis of the at least one rotation shaft.

10. The portable ultrasonic probe according to claim 9, wherein the first heat radiation module comprises:
    a heat spreader provided on a first surface of the transducer to absorb the heat generated by the transducer;
    a heat pipe provided to the heat spreader to transfer the heat absorbed by the heat spreader in a direction opposite to a direction in which the ultrasonic wave is projected; and
    a first connection portion provided to the heat pipe and thermally coupled to the second heat radiation module when the folder portion is in the first position to transfer heat transferred through the heat pipe to the second heat radiation module.

11. The portable ultrasonic probe according to claim 10, wherein the first heat radiation module further comprises at least one heat radiation plate provided to the heat spreader to emit the heat absorbed by the heat spreader.

12. The portable ultrasonic probe according to claim 10, wherein the first connection portion comprises a metal.

13. The portable ultrasonic probe according to claim 10, wherein the display portion is provided on a first surface opposite to a second surface of the folder portion which comes into contact with the main body when the folder portion is folded.

14. The portable ultrasonic probe according to claim 9, wherein the second heat radiation module comprises:
    a connection portion thermally coupled to the first heat radiation module when the folder portion is in the first position; and
    a heat radiation plate connected to the connection portion to emit heat transferred from the connection portion.

15. The portable ultrasonic probe according to claim 14, wherein the second heat radiation module further comprises a heat pipe configured to transfer heat absorbed by the connection portion to the heat radiation plate.

16. A portable ultrasonic probe comprising:
    a main body comprising at least one ultrasonic element configured to generate an ultrasonic wave;

a foldable part movable between a first position and a second position relative to the main body; and a hinge part configured to operatively connect the foldable part to the main body, wherein the hinge part is thermally coupled to the at least one ultrasonic element of the main body, wherein the hinge part comprises at least one rotation shaft such that the foldable part is rotated around at least one rotation shaft axis of the at least one rotation shaft.

17. The portable ultrasonic probe according to claim 16, wherein at least one from among the main body and the foldable part comprises a heat radiation plate thermally coupled to the hinge part.

18. The portable ultrasonic probe according to claim 16, wherein at least one from among the main body and the foldable part comprises a heat pipe thermally coupled to the hinge part and configured to transfer heat along a longitudinal direction thereof.

* * * * *